US005545897A

United States Patent [19]
Jack

[11] Patent Number: 5,545,897
[45] Date of Patent: Aug. 13, 1996

[54] OPTICALLY-BASED CHEMICAL DETECTION SYSTEM

[75] Inventor: Michael D. Jack, Goleta, Calif.

[73] Assignee: Santa Barbara Research Center, Goleta, Calif.

[21] Appl. No.: 322,447

[22] Filed: Oct. 4, 1994

[51] Int. Cl.$^6$ .......................... G01N 21/25; G01N 21/31
[52] U.S. Cl. ................... 250/339.13; 250/339.12; 250/343; 356/419; 356/436; 356/437
[58] Field of Search ...................... 250/339.02, 339.12, 250/339.13, 343, 345, 349, 373; 356/437, 438, 411, 414, 416, 419, 436, 439; 359/509, 512

[56] References Cited

U.S. PATENT DOCUMENTS

| | | | |
|---|---|---|---|
| 3,067,327 | 12/1962 | Scott et al. | 250/373 X |
| 3,860,344 | 1/1975 | Garfunkel | 250/339.13 X |
| 4,772,790 | 9/1988 | Aldridge | 250/343 |
| 4,829,183 | 5/1989 | McClatchie et al. | 250/339.13 X |
| 5,041,723 | 8/1991 | Ishida et al. | 250/343 X |
| 5,130,544 | 7/1992 | Nilsson | 250/339.13 X |
| 5,166,755 | 11/1992 | Gat | 356/419 |
| 5,210,702 | 5/1993 | Bishop et al. | 250/339.13 X |
| 5,254,858 | 10/1993 | Wolfman et al. | 250/349 X |
| 5,326,973 | 7/1994 | Eckerbom et al. | 250/343 |

FOREIGN PATENT DOCUMENTS 60-238746  11/1985  Japan ........................... 250/343

OTHER PUBLICATIONS

Article entitled "Analytical Approach—IR Long—Path Photometry: A Remote Sensing Tool for Automotive Emissions", by G. Bishop et al., in Analytical Chemistry 1989, 61, 617A.

Publication entitled "Find And Fix The Polluters", by James E. Peterson et al., Chemtech, Jan. 1992, pp. 47–53.

*Primary Examiner*—Carolyn E. Fields
*Assistant Examiner*—Edward J. Glick
*Attorney, Agent, or Firm*—W. C. Schubert; W. K. Denson-Low

[57] ABSTRACT

An in-situe chemical gas or fluid analyzer for vehicles, industrial, environmental and process control applications. As applied to a vehicle (1) having an internal combustion engine, the analyzer includes: (i) a source of electromagnetic radiation (14, 16); and (ii) a sampling cell (12) which collects emission gases of interest and which is capable of withstanding hostile environments while preserving a "clear" optical path between the sensor sampling cell and the source of radiation. The analyzer further includes: (iii) a solid state sensor (24, 26, 28, 30, 32) of monolithic construction which selectively detects electromagnetic radiation that is absorbed or emitted by one or more chemical species of interest, that compensates for temporal and spatial variations in illumination level provided by the source, and that provides an electrical signal output, in either analog or digital format, that is related to the measured concentrations. The sensor includes, in combination, a plurality of highly sensitive electromagnetic radiation detectors (26), spectral filters (24) which may utilize multiple layers of deposited dielectric thin films and/or selectively absorbing layers, and low noise electronics which performs a variety of functions including amplification (28), multiplexing (30), analog to digital (A/D) conversion (33), signal processing (32), and input/output (I/O). In a presently preferred embodiment each radiation detector is a thermopile detector that is integrated upon a common substrate with the support electronics and an associated optical bandpass filter.

46 Claims, 7 Drawing Sheets

OPTICALLY-BASED CHEMICAL DETECTION SYSTEM

FIELD OF THE INVENTION

This invention relates to a sensor for chemical detection in gas or liquid form that is applicable to principal or trace compound detection and under severe conditions of temperature or chemical corrosion.

BACKGROUND OF THE INVENTION

The accurate measurement of the composition of gas or liquid chemical streams by an in-situ spectrographic or spectro scopic system presents a number of challenges. By example, for a spectrographic system to be used aboard a vehicle the spectrographic system must be rugged and capable of operating in a hostile environment that is subject to wide fluctuations in temperature, and which furthermore may be periodically subject to extreme vibration. The spectrographic system should also preferably be of small size and low cost, while providing accurate and repeatable results; should include a minimum number of moving parts; should operate in a rapid, real-time manner, and should be simple to install, maintain and operate.

Three conventional approaches to measuring the composition of a stream of gas or liquid can be generally categorized as Fourier Transform Infrared (FTIR) Spectroscopy, Non-Dispersive Infrared (NDIR) Spectroscopy, and Diode Array or Scanned Dispersive Spectroscopy (SDS).

The FTIR system is a general purpose system that is capable of quantifying a variety of gases or liquids. However, the FTIR system typically includes moving optical components which may not be capable of providing real-time (i.e., less than one second) information regarding the molecular species concentration within a sample stream. This is due primarily to the time required to obtain an interferogram, and the time that is then required to convert the interferogram to molecular species concentrations. In general, the FTIR system is bulky, costly, and temperature-sensitive, making its use as an in-situe gas or liquid analyzer less than optimum.

The NDIR measurement system has been employed for sampling the exhaust gas plume from stationary vehicles by comparing the absorption of radiation along two different optical paths. A first, or reference path contains, by example, air; while a second, sample path may include a gas cell containing a specific gas, such as CO or $CO_2$, that is intended to be measured. Alternate approaches may utilize filters instead of gas cells. In either approach the conventional NDIR system, due at least to the requirement to provide two separate optical paths, is also bulky, costly, and may be temperature-sensitive, making its use as an in-situe emission analyzer less than optimum.

The SDS system utilizes an optical element, such as a grating, in combination with a mechanism for measuring and sequentially scanning a dispersed spectrum. Conventional systems are known to include a photodiode array used with parallel to serial multiplexing, or a mechanically translated photomultiplier. In general the SDS system is sensitive to vibration, and requires an accurate alignment of the integration and readout elements with the optical elements that disperse the spectrum.

Commonly assigned U.S. patent application Ser. No. 08/119,788, filed Sep. 10, 1993, (abandoned in favor of Ser. No. 08/318,566, filed Oct. 5, 1994), entitled "Optical Sensing Apparatus For Remotely Measuring Exhaust Gas Composition of Moving Motor Vehicles" by Michael D. Jack et al. teaches an IR-based system that measures the relative concentrations of several pollutants in the exhaust plume of a moving or a stationary vehicle. This system employs a number of adjacently spaced photodetectors that are sensitive to different wavelengths corresponding to spectral absorption peaks of constituents of the composition of the exhaust plume, including carbon monoxide, carbon dioxide, and hydrocarbons. This system is generally intended for roadside use, and not as an on-board component of a vehicle.

OBJECTS OF THE INVENTION

It is therefore one object of this invention to provide an in-situe spectral analyzer for determining the relative concentrations of molecular species in a gas or liquid stream, the spectral analyzer being rugged, of low cost, and of a small physical volume.

It is another object of this invention to provide a monolithic spectroscopic system for determining the relative concentrations of molecular species in a stream or flow of a gas or a liquid, wherein the monolithic construction overcomes or mitigates the sensitivity to temperature variations, vibration, and alignment accuracy that are inherent in the conventional, optically-based chemical species measurement systems.

SUMMARY OF THE INVENTION

The foregoing and other problems are overcome and the objects of the invention are realized by a robust, optically-based sensor system which samples and quantifies the composition/pollutant concentration in a gas or liquid stream. In an exemplary embodiment of this invention the sensor system is employed as an on-board emission gas analyzer for a vehicle having an internal combustion engine and includes: (i) a source of electromagnetic radiation; and (ii) a sampling cell which collects emission gases of interest and which is capable of withstanding hostile environments (i.e. corrosive environments, a high density of particulates, extreme vibration) while preserving a "clear" optical path between the sensor sampling cell and the source of radiation. The sensor system of this invention further includes: (iii) a solid state sensor of monolithic construction which selectively detects electromagnetic radiation that is absorbed or emitted by one or more chemical species of interest, that compensates for temporal and spatial variations in illumination level provided by the source, and that provides an electrical signal output, in either analog or digital format, that is related to the measured concentrations.

The sensor includes, in combination, a plurality of highly sensitive electromagnetic radiation detectors (for example, detectors that are responsive to the spectral range of 0.1 micrometers to 1000 micrometers), spectral filters which may utilize multiple layers of deposited dielectric thin films, a wavelength selective "dark" absorbing layer utilizing multiple layers of thin films, and low noise electronics which performs a variety of functions including amplification, multiplexing, analog to digital (A/D) conversion, signal processing, and input/output (I/O).

The sensor system has an optical interface between the source, sampling cell, and the sensor which is selected to withstand high temperatures and corrosive environments. This optical interface utilizes either free-space optics, optical fibers, or a combination of free-space optics and optical fibers.

A feature of the sensor system of this invention is its monolithic construction which provides a robust, modular, and manufacturable design. This makes the sensor system well suited for use as a low cost monitor of the composition of, or the pollutant concentration in, a variety of gas or liquid mixtures.

The sensor system of this invention may operate over a wide range of temperatures, is resistant to the presence of corrosive gases, is low cost, and is amenable for use in a wide range of applications including, but not limited to, vehicular applications (e.g., on-board emissions monitoring), environmental applications (e.g., air or water quality monitoring), and industrial applications (e.g., stack, fenceline or process control monitoring).

The sensor system of this invention employs somewhat similar physical principles as the above-described NDIR measurement system, but beneficially implements these functions entirely in a monolithic fashion, thereby ensuring uniform operating temperatures, small size, an ability to make measurements of multiple chemical species, and a potential for application specific and low cost manufacturing.

Applications of the teaching of this invention include, but are not limited to: In-situe process control; trace compound detection in processes; toxic waste site assessment: air or ground monitoring; industrial exhaust gas monitoring, i.e., in-situe stack monitoring; internal combustion engine exhaust sensors; humidity sensors for closed loop air conditioning; hybrid vehicle fuel reformers and exhaust monitoring; and electric car monitoring of toxic gas emissions from batteries.

BRIEF DESCRIPTION OF THE DRAWINGS

The above set forth and other features of the invention are made more apparent in the ensuing Detailed Description of the Invention when read in conjunction with the attached Drawings, wherein:

FIGS. 9a–9g are cross-sectional views, not to scale, that illustrate a method of fabricating a filled polymer thermopile detector that is compatible with a conventional integrated circuit fabrication process, while FIG. 9g is a top view of the completed thermopile detector;

DETAILED DESCRIPTION OF THE INVENTION

Figure 1:
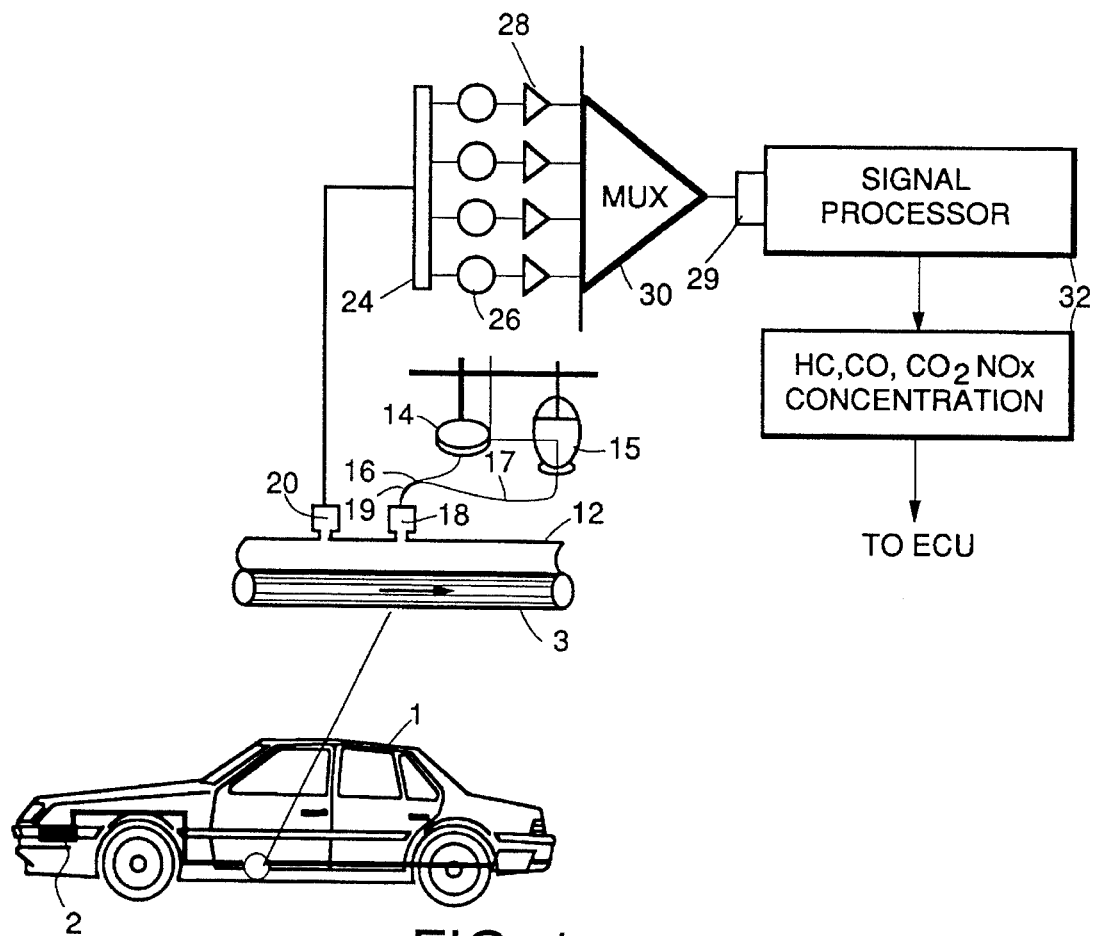
FIG. 1 is a system diagram of the sensor system of this invention used in an exemplary vehicle emissions monitoring application.

FIG. 1 is a system diagram of the spectrographic sensor system of this invention when used in an exemplary vehicle emissions monitoring application. In this embodiment the sensor system 10 is carried by a vehicle 1 and performs quantitative measurements of exhaust pollutants in real time. A sampling cell 12 is located at an intermediate temperature position between the vehicle's catalytic converter 2 and tailpipe 3. A broadband light source 14, such as a halogen lamp with an IR transparent envelope, is used to generate radiation within a band of wavelengths that are absorbed by the chemical species that it is desired to detect and quantify. The emitted radiation may be coupled through free space (as in FIG. 4) or, in the embodiment of FIG. 1, through an optical fiber 16 to an optical input port 18 of the sampling cell 12. The input port 18 may include suitable focusing optics. After passing through a sample of the exhaust gas that is obtained from the tailpipe 3 the radiation is extracted from the sampling cell 12 at an output port 20. The extracted radiation is routed to a high temperature optical fiber 22 or fiber bundle and is transmitted to the monolithic sensor assembly comprised of bandpass filters 24 and high sensitivity detectors 26. Each detector/filter pair, with the exception of a reference (REF) channel, is responsive to a predetermined range of wavelengths that corresponds to a spectral absorption characteristic of one of a chemical species that is desired to be detected. Each detector/filter pair converts radiation that is incident upon the detector into a voltage having a magnitude that is related to an amount of an associated chemical species (i.e., a major constituent or pollutant) in the exhaust gas stream. The voltage from each detector 26 is applied to amplifiers 28, an A/D converter 29, a multiplexer 30, and a signal processor 32 where the signals are converted to concentrations of pollutants, i.e., volatile hydrocarbons (HC); carbon monoxide (CO) and carbon dioxide ($CO_2$). Other pollutants, such as NO or $NO_2$, can be measured through the use of additional pairs of filters 24 and detectors 26. The output of the signal processor 32 is applied to a conventional Electronic Conditioning Unit (ECU) of the vehicle 1. The ECU is not illustrated in FIG. 1, as the operation of same forms no part of this invention.

Figure 2:
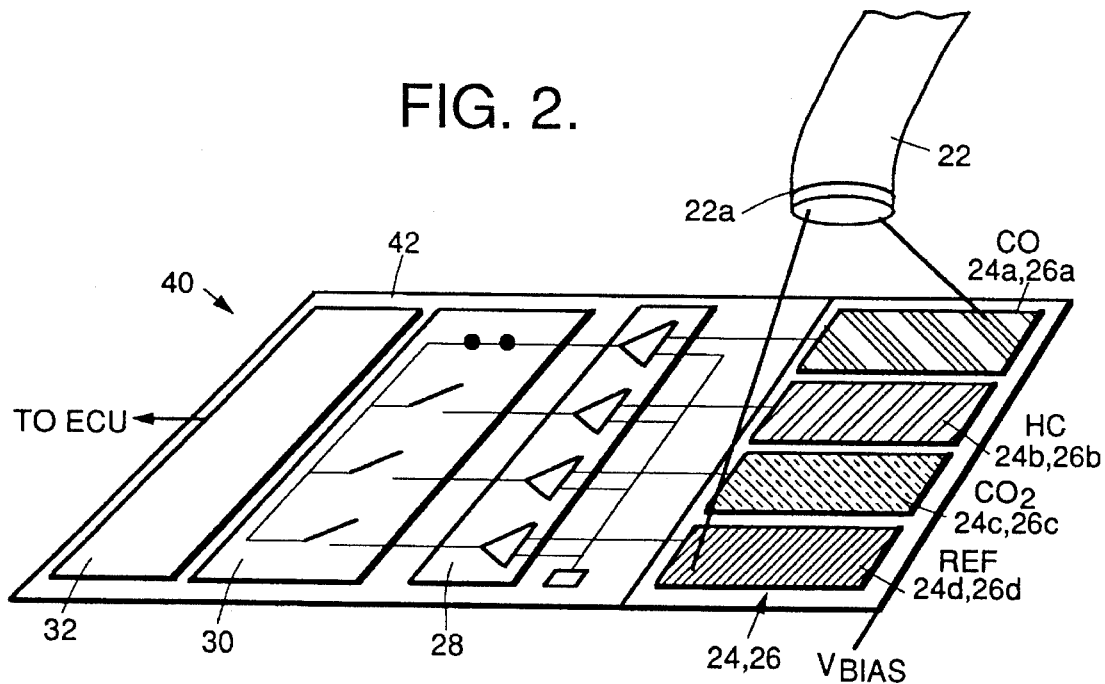
FIG. 2 is an elevational view, partly in block diagram form, of a monolithic integrated sensor in accordance with this invention for determining the composition of a gas of liquid.

FIG. 2 depicts the monolithic integrated sensor 40 of this invention which comprises the bandpass filters 24, the associated detectors 26, the amplifiers 28, the multiplexer 30, A/D converter 29, signal conditioners, and the signal processor 32 of FIG. 1.

In the illustrated embodiment the monolithic sensor 40 includes four separate detector/filter pairs, one at a reference (REF) wavelength, one for CO, one for Hydrocarbons, and one for CO2. Each filter 24 is disposed upon a radiation receiving surface of an associated detector 26, which are in turn disposed upon or within a surface of a substrate 42, such as a planar body of silicon. The terminal end of the optical fiber 22, which delivers radiation that passes through the sampling cell 12 of FIG. 1, preferably includes a diffuser 22a for spatially spreading the output radiation so that all four of the filter/detector pairs are uniformly illuminated. The amplifiers 28, shown schematically, are integrated onto the silicon substrate 42. The outputs of the amplifiers 28 are multiplexed, converted to digital, and are then passed to the signal processor 32. The output of the signal processor 32, which represents the determined concentrations of the chemical species of interest, is subsequently passed in bit serial format to the ECU. This technique reduces the required I/O to three signals lines (power, ground and bit serial signal).

The multiplexer 30 preferably is repetitively clocked so as to output the amplifier signals in turn. By example, a complete multiplexer cycle can occur in less than one second, with each amplifier 28 output being presented to the input of the A/D for 0.2 seconds. In this case the signal processor 32 is aware of the current phase of the multiplexer clock and thus is also aware of which spectral channel output is being presented. Alternately, the signal processor 32 can directly control the operation of the multiplexer 30 through the use of multiplexer input select signal lines, in a manner well known in the art.

It should be realized that in some embodiments of the invention it may be desirable to modify the ECU to perform the concentration calculations, as described below, instead of the signal processor 32. In this case the output of the A/D converter may be serialized and passed directly to the ECU.

Figure 3:
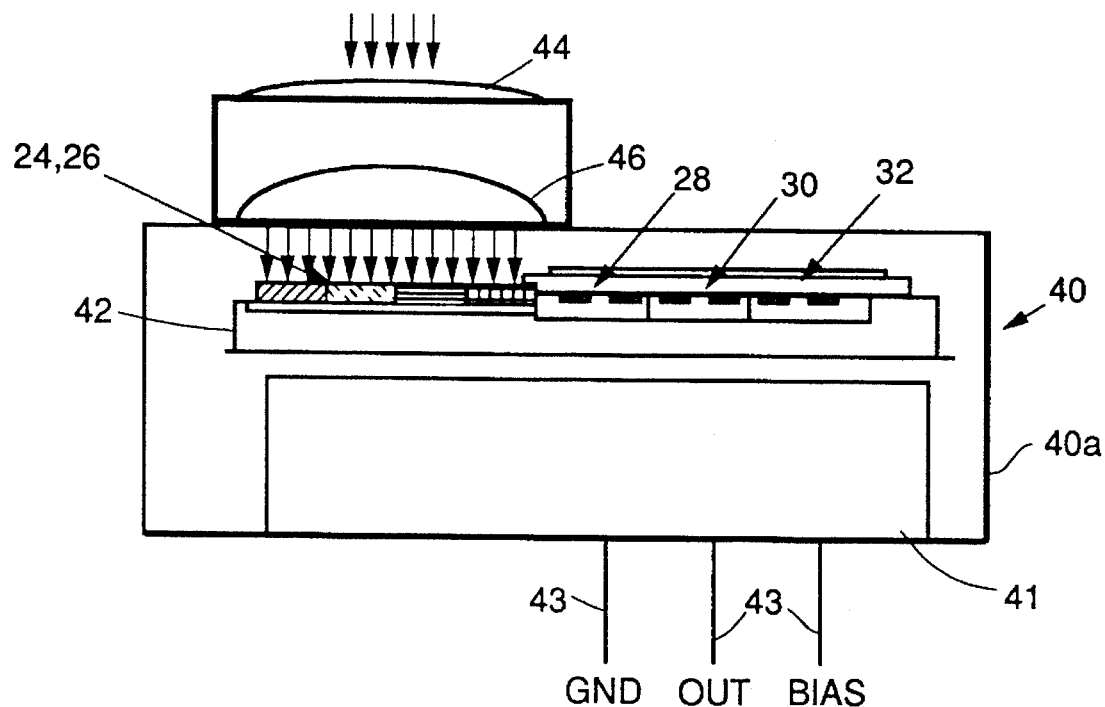
FIG. 3 is a simplified cross-sectional view, not to scale, illustrating the sensor with a beam integrator, detectors, and associated circuits all contained within a conventional TO5 package.

The embodiment of FIG. 2 is amenable to being packaged conventionally, i.e., using a TO5 package or can 40a, as illustrated in FIG. 3. The sensor 40, more particularly the substrate 42, is affixed to a header 41 and is wire-bonded to a plurality of I/O leads or terminals 43. The upper surface of the can 40a has an opening to which is affixed an optical input assembly comprised of a focussing lens 44 and a beam integrator or diffuser 46. If used with the fiber optic of FIG. 2 the optical input assembly may include a suitable fiber optic termination.

Figure 4:
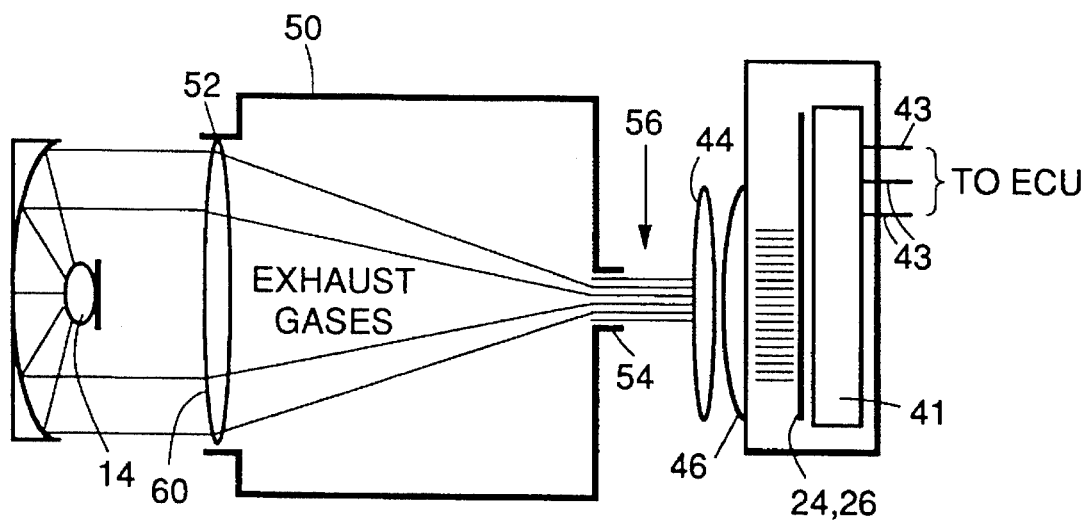
FIG. 4 is a simplified cross-sectional view, not to scale, of a further embodiment of the sensor system showing an optical source, an exhaust sampling cell, and a sensor.

An alternate embodiment of this invention, illustrated in FIG. 4, directly couples the source 14 through free-space to an optical input port 52 of a sampling cell 50. An optical output port 54 of the cell 50 is coupled to the input ends of a fiber optic bundle 56. The output ends of the fiber optic bundle 56 are coupled to input of the TO5 sensor assembly that is illustrated in FIG. 3. The optical source 14 is provided with a collimating mirror 58 and a focussing lens 60 to provide a focussed wideband optical beam that traverses the interior volume of the sampling cell 50 before illuminating the input ends of the fiber optic bundle 56.

The vehicle exhaust gases that are present within the sampling cell 50 selectively absorb different bands of wavelengths that are output from the broadband source 14. The specific absorption bands are a function of the chemical species that are present within the exhaust gas, while the amount of absorption within a given band is a function of the concentration of the associated absorbing chemical species within the exhaust gas. The partially absorbed radiation is coupled, via the fiber optic bundle 56, to the filter/detector pairs (24, 26) of the sensor 40 where the amount of absorption within selected ones of the wavelength bands is measured.

The sensor system of this invention can be configured to accommodate a variety of wavelengths and, hence, different chemical species. For example, the embodiment illustrated in FIG. 2 can employ four filter/detector pairs in the infrared region (for example, within the range of approximately one micrometer to approximately 15 micrometers), or mixtures of detector/filter pairs sensitive at shorter wavelengths (for example, the ultraviolet (UV) and visible wavelengths) or longer wavelengths. By example, the chemical species NO exhibits absorption peaks that enable it to be sensed in either the IR, UV or VLWIR wavelength bands.

Referring again to FIG. 1, it is within the scope of this invention to provide an optical source that outputs radiation within two distinct wavelength bands, such as the IR (source 14) and the UV (source 15 and associated fiber optic 17). In FIG. 1 the separate UV and IR sources are combined through optical diffractive and/or reflecting optics to pass through a common optical fiber or fiber bundle 19. In this case it may be desirable to employ the UV radiation for determining the concentration of NO, while the IR radiation is used for the other chemical species of interest, and also for the REF channel.

Figure 5:
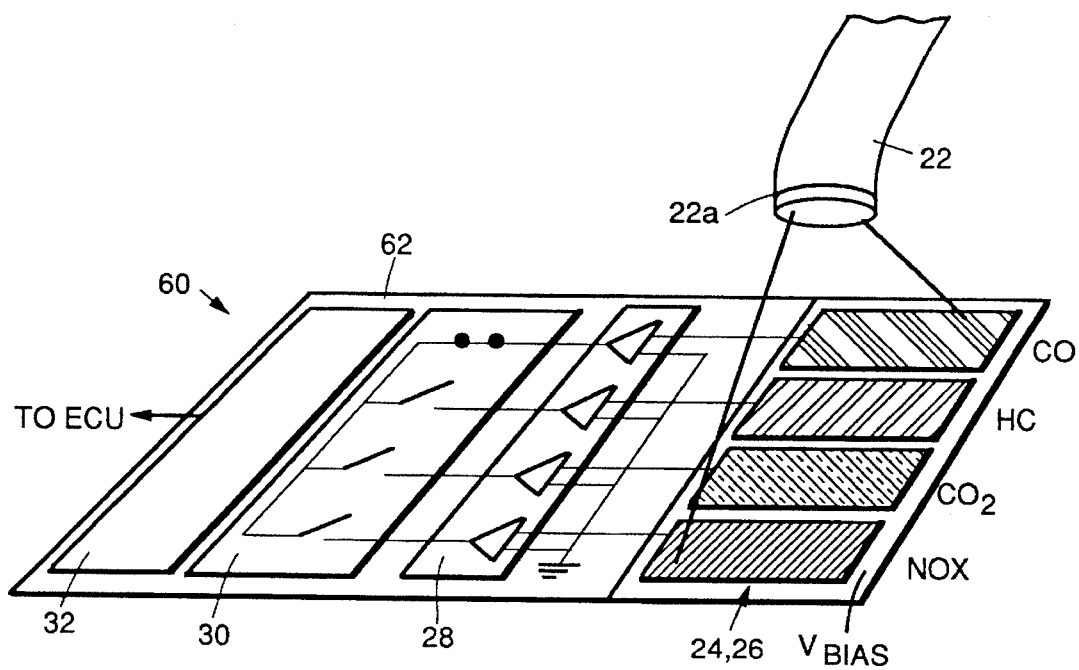
FIG. 5 is an elevational view, partly in block diagram form, of a monolithic integrated sensor in accordance with this invention that utilizes spectral absorption in widely separated regions (MWIR and UV) of the electromagnetic spectrum.

By example, the monolithic embodiment of the sensor assembly 60 shown in FIG. 5 utilizes the single fiber 22 or fiber bundle 56 to illuminate chemically specific filter/detector combinations. In this embodiment there are three mid-wave (3–5 micrometers) IR-responsive filter/detector pairs (CO, HC, $CO_2$), and one UV-responsive filter/detector pair (for $NO_x$).

The spectral regions that may be utilized by various embodiments of this invention include, but are not limited to, the UV (below approximately 0.4 micrometers), the visible (approximately 0.4–0.8; micrometers), short wavelength IR (SWIR, approximately 0.8–3 micrometers), mid-wavelength IR (MWIR, approximately 3–8 micrometers), long wavelength IR (LWIR, approximately 8–12 micrometers), very long wavelength IR (VLWIR, approximately 12–20 micrometers), and the far IR (FIR, approximately 20–1000 micrometers).

Further in accordance with this invention the sampling cell 12 is provided with one or both of a mechanism for retarding an accumulation of an emission gas constituent upon the transparent window portion, and a mechanism for removing an accumulation of an emission gas constituent from the window.

Figure 6:
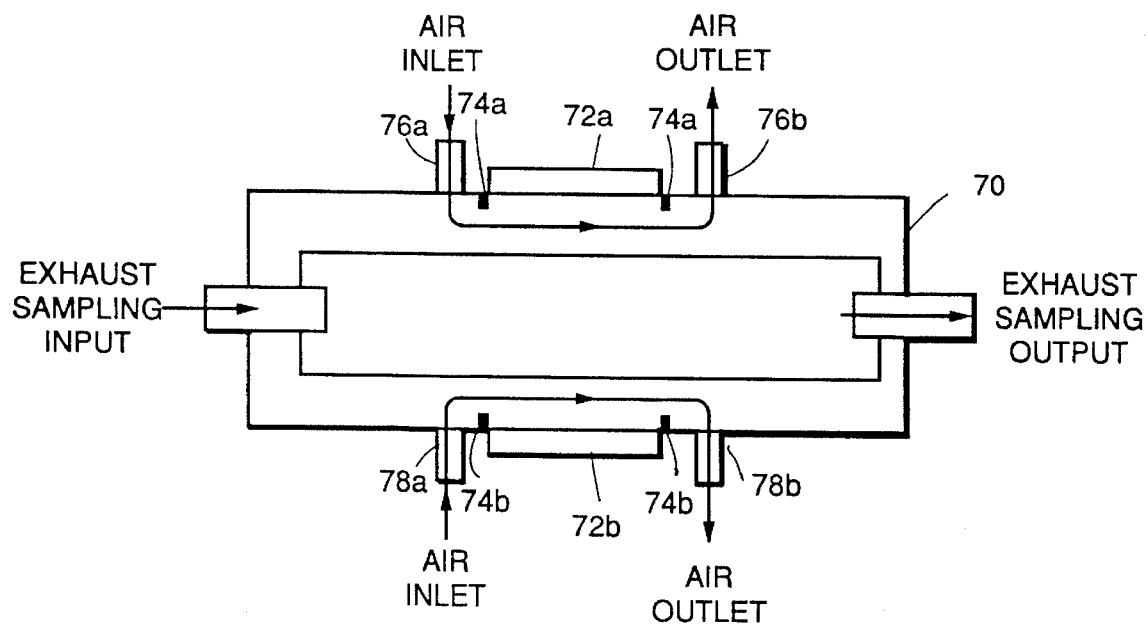
FIG. 6 is a simplified cross-sectional view, not to scale, that illustrates a sampling cell of this invention having recessed window portions and a protective air flow to shield the windows from contact with particulates in a sampled exhaust gas stream.

More particularly, FIG. 6 is a simplified cross-sectional view, not to scale, that illustrates a sampling cell 70 of this invention having recessed window portions 72a and 72b with baffles 74a and 74b that provide a protective air flow to shield the window portions from contact with particulates in the exhaust gas emission. A goal of this embodiment of the sampling cell 70 is to provide and maintain a clear optical path over an assumed 100,00 mile lifetime of the vehicle that includes the sensor system, even in the presence of moderate to heavy particulate densities in the exhaust gas stream. The recessed window portions 72a and 72b, in combination with baffles 74a and 74b, air inlets 76a and 76b, and air outlets 78a and 78b, provide a controlled air flow, i.e. a "Bernouilli" layer, to protect the surfaces of the IR transparent windows from carbon depositions.

Figure 7A:
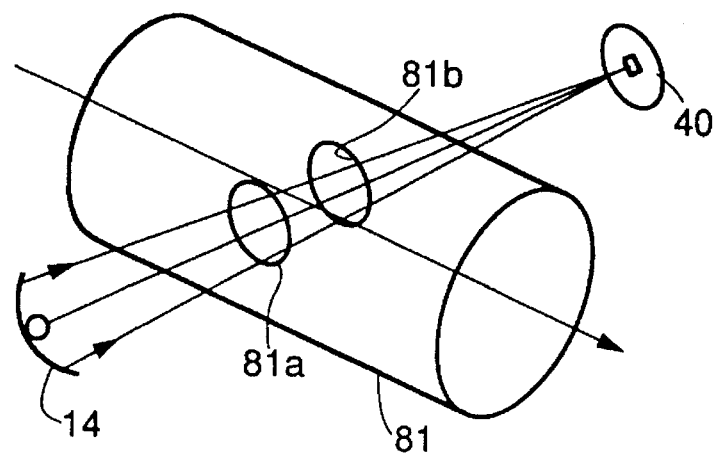
FIG. 7a shows the sampling cell utilizing apertures as windows.
Figure 7B:
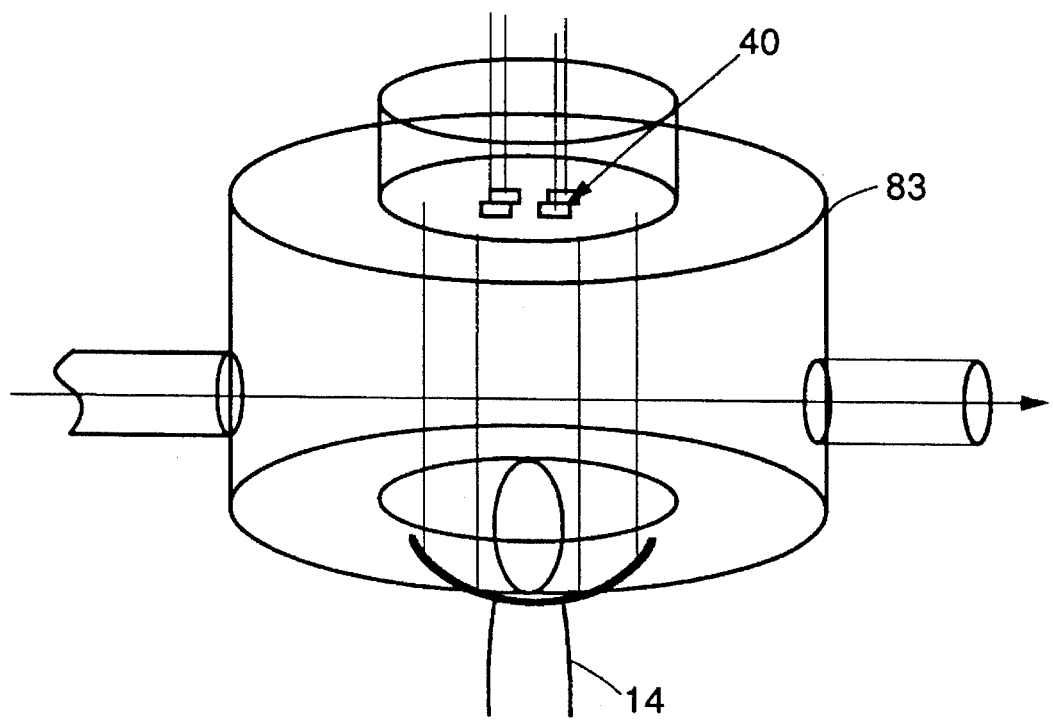
FIG. 7b shows the source and detector array located within the sampling cell.
Figure 7:
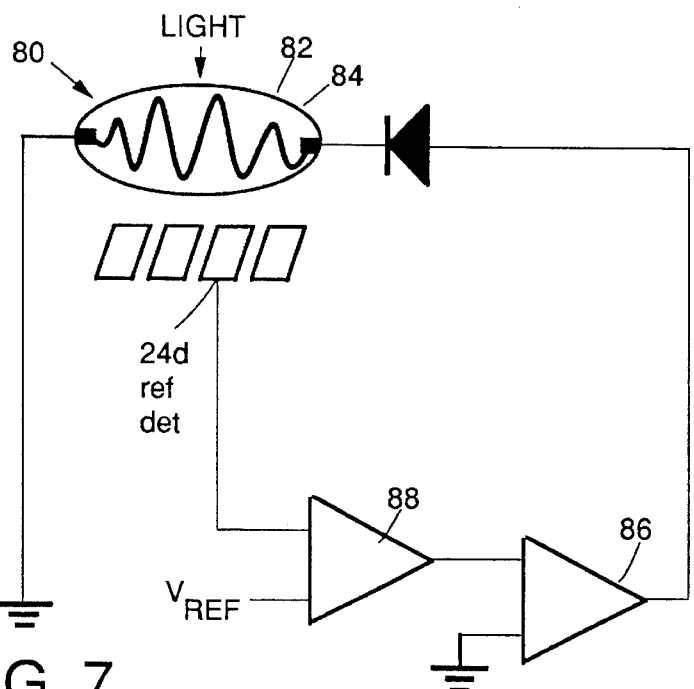
FIG. 7 is a schematic diagram that illustrates a self-cleaning IR-transparent window that is one feature of this invention.

FIG. 7 is a schematic diagram that illustrates a further embodiment of a sampling cell 80, specifically one having a self-cleaning IR-transparent window 82. In this embodiment the window 82 includes a thin film heater, such as a thin film resistor 84, that is periodically energized to heat the window 82 to above the approximately 600° C. ignition temperature of the (principally) carbon depositions that accumulate on the window 82. This is a regenerative procedure that is triggered by an apparent reduction in the illumination level of the reference detector 24*d* (FIG. 1). A high current is generated by a power amplifier 86 when a sense amplifier 88 detects that the output of the reference detector 24*d* falls below a predetermined level set by a reference voltage ($V_{ref}$). The output of the power amplifier 86 may be applied through a half-wave rectifying diode 90 and thence to the thin film resistor 84, thereby heating the window 82 to temperatures above the 600° C. ignition temperature of the carbon deposits. When a sufficient amount of the carbon deposit has been burned away the output of the reference detector 24*d* rises above the threshold set by $V_{ref}$, thereby turning off the power amplifier 86.

It may be desirable to provide some degree of hysteresis so as to keep the thin film resistor 84 energized for a set period of time (for example, 10 seconds) after the reference detector output increases above the threshold set by $V_{ref}$. This insures that a significant portion of the carbon deposit is burned away, and thus avoids a situation where the IR transmissivity of the window 82, as determined from the output of the reference detector 24*d*, is operated very close to the level set by the reference voltage $V_{ref}$.

FIG. 7*a* illustrates in a partially transparent manner an embodiment of this invention wherein the windows are dispensed with and wherein a sampling cell 81 has a plurality of opposed openings or apertures 81*a* and 81*b*. In this embodiment light from the source 14 is directed through the apertures 81*a* and 81*b*, and thence through the exhaust stream, to the monolithic detector assembly and associated electronics.

FIG. 7*b*. illustrates an embodiment wherein a sampling cell 83 encloses the source and detector assemblies, thereby also eliminating a requirement for providing windows within the sampling cell. The embodiments of FIGS. 7*a* and 7*b* both circumvent a need to remove, or avoid the buildup, of deposits on windows.

In an unillustrated embodiment of the exhaust sampling cell a filter can be employed to trap carbon particles from the exhaust gas stream. In this embodiment the filter is periodically heated to the flash point of the carbon particles which it entraps.

In another embodiment a programmable sampling valve, such as a butterfly valve, enables periodic sampling of the exhaust gas stream to reduce the total amount of time that the sampling cell is directly connected to the exhaust stream.

In certain of these embodiments of this invention the IR transparent window(s) may be specially coated with a layer of material that is selected to minimize the adherence of carbon particles. One suitable IR-transparent coating material is a thin layer of diamond. Another suitable coating material is magnesium fluoride. It is also within the scope of the invention to employ various high-temperature polymers, so long as the selected polymer is substantially transparent at the range of wavelengths generated by the source(s) 14 and 15.

Furthermore, any of the embodiments can also employ a cooling trap to condense water vapor and also relatively large hydrocarbon particles from the exhaust gas stream.

It should be realized that the exhaust gas sampling cell of this invention may employ features from several of the foregoing embodiments. For example, a sampling cell can include the controlled window-purging air flow of FIG. 6 in combination with the heated window of FIG. 7, and also a cooling trap connected to the input sampled exhaust gas stream.

Suitable dimensions for all of the various embodiments of the sampling cell disclosed thus far are a length of approximately 10 cm and a diameter that is comparable to the length.

Figure 8:
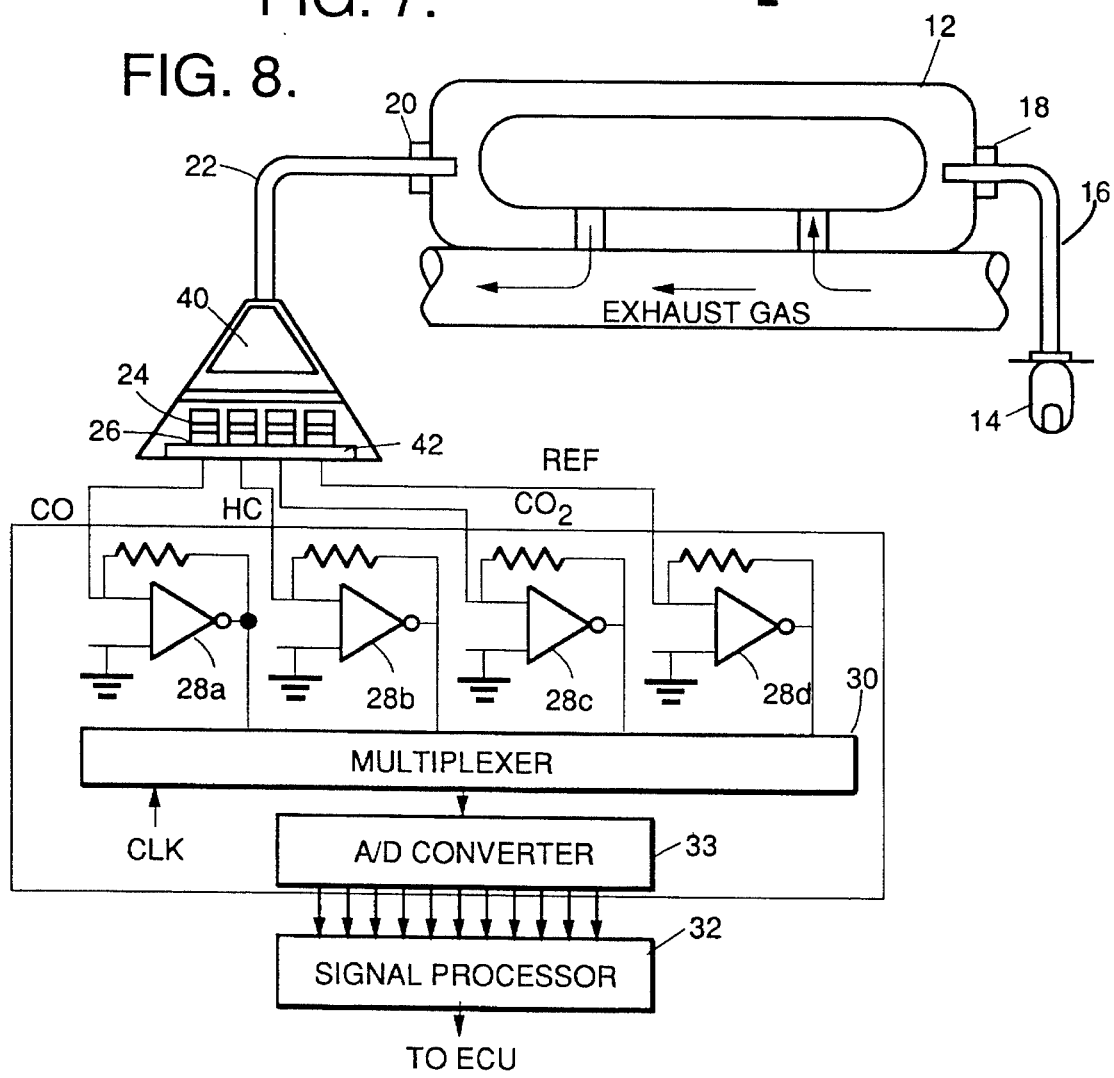
FIG. 8 is a schematic diagram illustrating low noise electronics for amplification, multiplexing and A/D conversion.

FIG. 8 is a schematic diagram illustrating one embodiment of low noise electronics for amplification, multiplexing and A/D conversion of the filter/detector pair outputs. Each chemical species responsive channel, including the reference channel, has an associated low noise amplifier 28*a*–28*d*. The four channels are selectively applied through the multiplexer 30 and to an A/D converter 33. The digital output of the A/D 33 may be serialized before being fed to the ECU of the vehicle, or may be applied in parallel to the signal processor 32 if same is integrated with the other electronics upon the monolithic sensor assembly substrate.

In a presently preferred embodiment of this invention the A/D 33 is implemented as a successive approximation A/D constructed in a high temperature bipolar technology. Low noise integrated chopper stabilized amplifiers are preferably employed to implement the amplifiers 28*a*–28*d*, using MOS components that minimize drift while obtaining high gain and low noise over the required bandwidth and operating temperatures. As a result, the monolithic sensor assembly employs conventional BIMOS integrated circuit fabrication techniques. If the signal processor 32 is also integrated onto the sensor assembly then either MOS or bipolar technology can be employed in its fabrication, although the use of MOS circuits are preferred because of the smaller power requirement.

A suitable amplifier bandwidth is typically less than 10 Hz. Typical performance specifications for these integrated components include an operating temperature range of –50° C. to 125° C.; an input-referred noise of less than 1 μV; an offset voltage drift of less than 0.3 μV/C; and an offset current drift of less than 1 pA/C. These parameters are consistent with low noise detector amplification and fabrication practice.

The detectors 26 are preferably comprised of high detectivity (sensitivity) materials, and are also preferably fabricated on the common substrate 42 (62) with the associated electronics, as depicted in FIGS. 2 and 5. Suitable examples include, but are not limited to, cooled photoconductive HgCdTe or InSb detectors; or uncooled detectors such as those based on bolometers, thermopiles, pyroelectric, and Pb-Salt detectors. Photovoltaic detectors may also be used.

In a presently preferred embodiment of this invention each of the detectors 26*a*–26*e* (FIGS. 1 and 5) is a thermopile detector constructed in accordance with a method disclosed in commonly assigned U.S. patent application Ser. No. 08/322,442, filed Oct. 4, 1994, entitled "Integrated Thermopile Sensor for Automotive, Spectroscopic and Imaging Applications, and Methods of Fabricating Same" which was filed in the name of the inventor of this patent application.

A thermopile is comprised of a plurality of thermocouples that are connected in series. Each thermocouple relies on the generation of the well known Thomson and Peltier emfs that result from a temperature gradient across a junction between two dissimilar metals. A combination of the Thomson and Peltier effects produce the Seebeck emf which is used in thermocouples.

In general, a thermopile radiation receiver has a first set of junctions (hot junctions) that make good thermal contact with a radiation receiver (e.g., a black body) but which are electrically insulated from the radiation receiver. A second set of junctions (cold junctions) are attached to a support which does not receive the radiation and which is therefore at a lower temperature. The incident radiation raises the temperature of the radiation receiver and produces a voltage output from the thermopile that is proportional to the energy absorbed. That is, the thermopile output voltage is proportional to a temperature difference and is, therefore, proportional to the total radiation energy received.

Figure 9A:
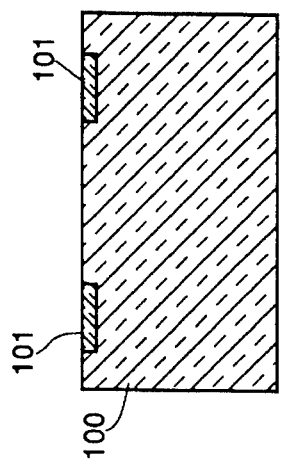
Figure 9B:
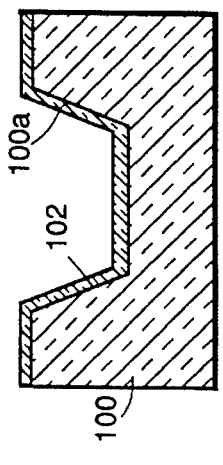
Figure 9C:
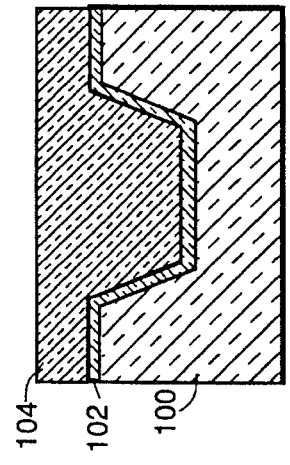
Figure 9D:
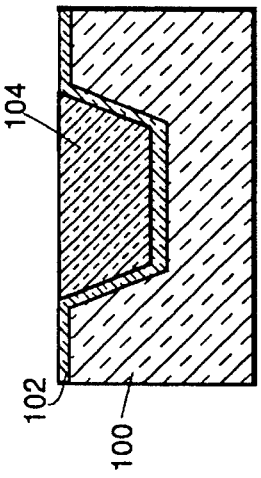
Figure 9E:
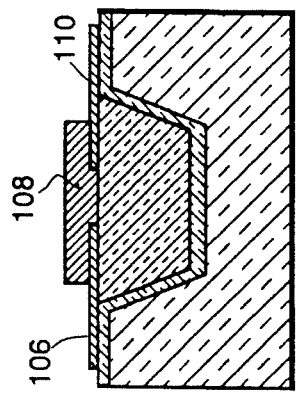
Figure 9F:
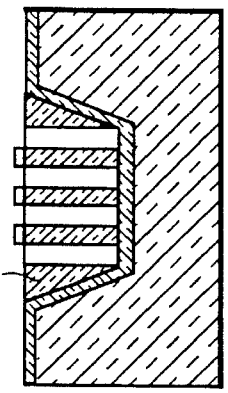
Figure 9G:
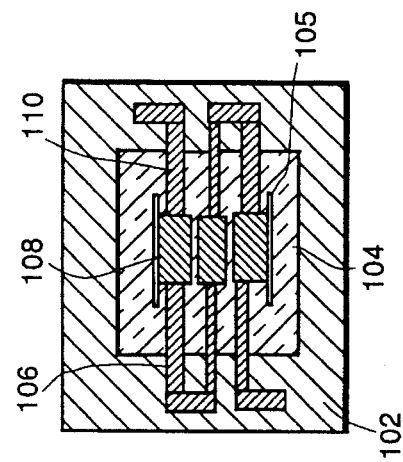

An example of a novel silicon-based, frontside illuminated thermal (IR) detector 26 utilizing a polymer for thermal isolation is shown in FIGS. 9a–9g. Processing begins by fabrication of silicon circuits 101 in a silicon substrate 100 using a BIMOS process. These circuits include: the associated amplifier 28, multiplexer 30, and other support electronics, such as the signal processor 32. Then a hole or recess 100a is etched into the substrate 100. The recess 100a may have a depth of 100 micrometers, and a lateral extent that is also 100 micrometers. Next a thin layer of silicon oxide is grown over the surfaces of the substrate and recess 100a. In FIG. 9c the oxide covered recess 102 is filled with a low thermal conductivity polymer 104, such as a spun-on polyimide, and in FIG. 9d the structure is planarized with a suitable wet or dry etch. This step leaves the oxide covered recess 100a filled with the polymer 104, and the oxide coating 102 exposed upon the top surface of the substrate 100. In FIG. 9e suitable masks are applied and Bi, Au, and Sb metalization (106, 108, 110, respectively) is deposited over the oxide coating (cold junctions) and also over the polymer-filled recess (hot junctions). In FIG. 9f a mask is applied and trenches are etched through the polymer 104, between the deposited metalization, so as to further reduce the thermal conductivity of the polymer 104. A single layer or multilayer "dark" coating or film 105 can be applied (by thin film deposition and delineation) to the completed thermopile detector to selectively absorb electromagnetic radiation within a given band. One suitable, but not limiting, material system for forming the dark film 105 is Ti/ZnSe. FIG. 9g is a planar view of the completed detector 24.

Next, the bandpass filter 24 is deposited over the detector 26 as a multi-layered dielectric stack having multiple layers of, by example, zinc sulfide (ZnS). The multi-layered filter 24 has a passband characteristic that corresponds to the desired range of wavelengths to be detected. The desired range of wavelengths are those that correspond to the selected absorption peak of the chemical species to be detected by the detector 26. Techniques for specifying and fabricating multi-layered optical filters are well known in the art.

By example only, the NO spectral channel has a filter 24 with a passband centered on 5.26 micrometers, the $CO_2$ spectral channel has a filter 24 with a passband centered on 4.2 micrometers, the CO spectral channel has a filter 24 with a passband centered on 4.6 micrometers, the HC spectral channel has a filter 24 with a passband centered on 3.3 micrometers, and the reference (REF) channel has a filter with a passband centered on 3.8 micrometers. All of the foregoing wavelengths have an associated tolerance of, by example, ±3% with the exception of the NO channel which is much narrower (−0.5%). For a UV-based $NO_x$ channel the associated filter has a passband centered on, by example, 227 nanometers.

In general, the reference (REF) spectral channel is provided at a region in which no emission gases strongly absorb the source radiation, and is used to compensate the other spectral channels for variations caused by fluctuations in the output of the IR source 14, any obscuring particulate matter in the exhaust gas stream, and any other factors that may reduce the amount of illumination reaching the detectors 24 (such as carbon buildup on the IR transparent window of the sampling cell). The REF spectral channel thus operates to provide a baseline output which is independent of the molecular species (CO, HC, $CO_2$, NO) being measured. The output of the REF spectral channel is used to normalize, such as by dividing, the other molecular species spectral channels.

It is also within the scope of this invention to employ an NO channel that is compensated for water vapor absorption, as described in commonly assigned U.S. patent application Ser. No. 08/239,151, filed May 5, 1994, (now U.S. Pat. No. 5,418,366), entitled "IR-Based Nitric Oxide Sensor Having Water Vapor Compensation" and which was filed in the name of the inventor of this patent application and also in the name of Lane H. Rubin. In this case an $H_2O$ spectral channel is also provided, the $H_2O$ channel having a filter with a passband centered on, by example, 5.02 micrometers. The output of the $H_2O$ channel is employed by the signal processor 32 to compensate and correct the NO channel for absorption that results from water vapor.

Exemplary dimensions for each of the detectors 26 are approximately 1×1 millimeter, although the invention is not so limited. These dimensions are sufficiently large so as to accommodate the filters 24 while still achieving a high signal-to-noise ratio. The integral design of the sensor assembly, especially the detectors 26 and filters 24, ensures that the sensors operate isothermally, thereby eliminating inaccuracies resulting from temperature differences. If required, the temperature of the detectors 26 can be regulated by a suitable temperature controller.

Since the exhaust gas may be diluted by air injected into the catalytic converter, it is preferred to calibrate and normalize pollutant concentrations with respect to a major combustion constituent, such as CO.

The concentrations of $CO_2$, CO and HC as functions of the transmittances of the respective wavelengths of light, as sensed by the associated detectors 26, can be computed in a manner similar to that disclosed in an article entitled "ANALYTICAL APPROACH—IR Long-Path Photometry: A remote Sensing Tool for Automotive Emissions:, by G. Bishop et al, in Analytical Chemistry 1989, 61, 617A. As described in this article, an infrared beam is transmitted through the exhaust plume of an automotive vehicle to a sensor unit which includes a beam splitter which splits the beam into a carbon dioxide ($CO_2$) channel and a carbon monoxide (CO) channel.

Figures 10, 11:
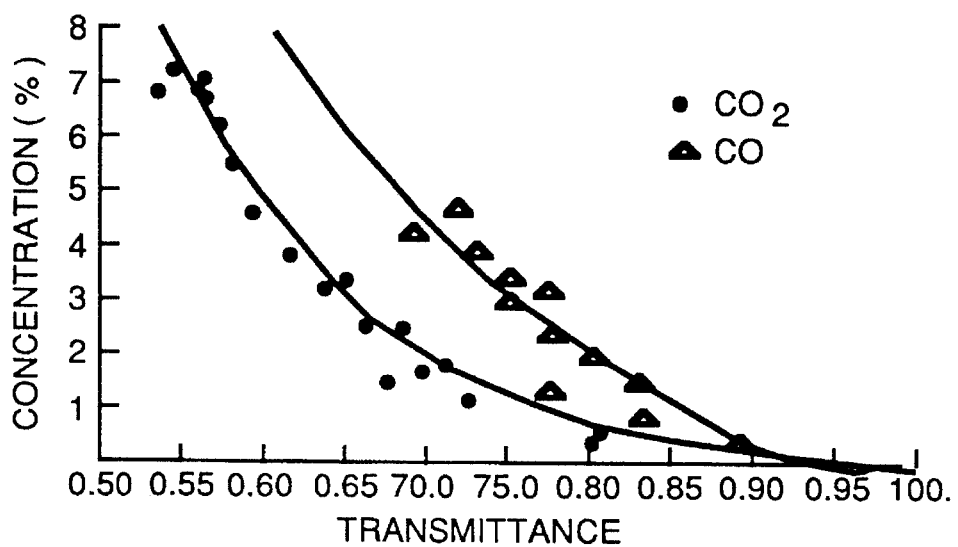
FIG. 10 is a graph illustrating a relationship between optical transmittance and exhaust gas composition.
FIG. 11 is a graph illustrating a relationship between carbon monoxide concentration and carbon dioxide concentration.

In the instant invention, the transmittance of the radiation through the exhaust gas contained within the sampling cell varies with constituent concentration in a generally non-linear manner as illustrated in FIG. 10.

The illustrated curves for $CO_2$ and CO were obtained experimentally over an absorption pathlength of 203 millimeters, and can be used for reference purposes. A similar curve, not shown, exists-for HC. The CO vs. $CO_2$ 5 ratio can be expressed as the slope of a line "A" (FIG. 11) which can be computed by, for example, linear regression analysis of the individual data samples obtained over the sampling interval.

The parameters which are sensed directly by the sensor system 10 of this invention are concentration-pathlength products of the constituents. A percentage constituent concentration can be calculated with sufficient accuracy for practical use using the stoichiometric chemical relationships of the combustion process. A preferred example of such a computation for practicing the present invention is as follows.

The constituent concentrations in a nominal absorption pathlength of 10 centimeters is calculated using curves such as those illustrated in FIG. 10. Calibration is initially performed in the factory using a standard source gas with known concentrations of CO, HC and $CO_2$. The initial factory calibration can be updated in the field, if necessary, using the standard gas source and by directly injecting the sample gas into the sampling cell 12.

The standard source gas is released into the optical beam within the sampling cell 12 and the transmittances $T_{CO}$, $T_{HC}$ and $T_{CO2}$ are measured. The concentration-pathlength product for the CO contained in the gas is determined from the measured transmittance $T_{CO}$. The measurement of concentration-pathlength product is determined repeatedly using different mixtures of the calibration gas with known amounts of diluent (such as air) released into the beam.

For each measurement of the- concentration-pathlength product for CO, the concentration-pathlength product for HC and $CO_2$ is determined based on the measured concentration-pathlength product of CO and the known ratios of HC/CO and $CO_2$/CO in the standard source gas, reduced by the diluent ratio.

From the measured transmittances $T_{HC}$ and $T_{CO2}$, and the concentration-pathlength products determined for HC and $CO_2$, the relationships between transmittance and pathlength-products (such as those shown in FIG. 10), can be quickly determined for HC and $CO_2$.

For measurements of $CO/CO_2$ and $HC/CO_2$ in the exhaust gas sample that is present within the sampling cell 12, the transmittances $T_{CO}$, $T_{HC}$ and $T_{CO2}$ are measured directly and concentration-pathlength products for CO, $CO_2$ and HC are determined from the relationships shown in FIG. 10 that result from the calibrations described above. Absolute concentrations of CO, HC and $CO_2$ are then calculated using the following formulas:

$$\%CO_2 = 42/(2.79 + 2S_{CO} - 0.37S_{HC});$$

$$\%CO = \%CO_2 \times S_{CO}; \text{ and}$$

$$\%HC = \%CO_2 \times S_{HC};$$

and are subsequently output to the ECU.

The derivation of $\%CO_2$ is based on a stoichiometric chemical balance in the combustion process using a "nominal fuel" having a carbon vs hydrogen ratio of 1.8.

While the invention has been particularly described with respect to preferred embodiments thereof, it will be understood by those skilled in the art that changes in form and details may be made therein without departing from the scope and spirit of the invention.

For example, although the filters 24 have been described as being deposited upon the detectors 26 in the highly integrated and monolithic sensor embodiment, it is within the scope of this invention to separately fabricate the filters upon a transparent substrate, and to subsequently bond or otherwise couple the filters to their respective detectors. In like manner more or less than four spectral channels can be employed, and chemical species other than those specifically detailed above can be detected and their concentrations quantified.

As such, the various embodiments of this invention that have been detailed above are not to be construed in a limiting sense upon the practice of this invention.

What is claimed is:

1. A vehicle that generates a gas comprised of a plurality of different chemical species, the vehicle comprising:
    means for sampling at least a portion of the gas, said sampling means having an optical input port and an optical output port;
    an optical source having an output coupled to said optical input port of said sampling means, said optical source generating electromagnetic radiation having wavelengths that are absorbed by predetermined ones of the chemical species; and
    a plurality of radiation detector means individual ones of which have an input coupled to said optical output port of said sampling means, individual ones of said radiation detector means comprising an integral input filter for passing wavelengths within a band of wavelengths and being responsive to the band of wavelengths, that includes wavelengths that are absorbed by at least one of the predetermined ones of the chemical species, for determining an amount of the electromagnetic radiation, within the band of wavelengths, that is transmitted through the gas within said sampling means, wherein individual ones of said input filters are deposited upon a radiation receiving surface of an associated one of said radiation detector devices.

2. A vehicle as set forth in claim 1 and further comprising processor means having an input coupled to an output of said plurality of radiation detector means for determining a concentration of the predetermined ones of the chemical species within the gas.

3. A vehicle as set forth in claim 1 wherein individual ones of said radiation detector means are comprised of a radiation detector device that is fabricated within or upon a surface of a substrate, and further comprising a plurality of amplifier circuits individual ones of which have an input coupled to an output of one of said radiation detector devices, said plurality of amplifier circuits being fabricated within or upon the surface of said substrate.

4. A vehicle as set forth in claim 1 wherein individual ones of said integral input filters is comprised of a multi-layered filter that is deposited upon said radiation receiving surface of said radiation detector device.

5. A vehicle as set forth in claim 3 wherein individual ones of said radiation detector means are further comprised of a selectively absorbing film deposited upon a radiation receiving surface of said detector device.

6. A vehicle as set forth in claim 1 wherein individual ones of said radiation detector means are comprised of a thermopile radiation detector that is fabricated within or upon a surface of a substrate.

7. A vehicle as set forth in claim 1 wherein said optical source generates electromagnetic radiation having wavelengths within a least one spectral band selected from the group consisting of the ultraviolet spectral band, the visible spectral band, the infrared spectral band, and the far infrared spectral band.

8. A vehicle as set forth in claim 1 and further comprising means, coupled to said output port, for diffusing electromagnetic radiation passing through said output port.

9. A vehicle as set forth in claim 1 wherein said sampling means is comprised of a sampling cell having at least one window that is substantially transparent to the electromagnetic radiation having wavelengths that are absorbed by predetermined ones of the chemical species.

10. A vehicle as set forth in claim 9 and further comprising means for retarding an accumulation of an emission gas constituent upon said window.

11. A vehicle as set forth in claim 1 wherein said sampling means has a plurality of apertures for forming said input port and said output port.

12. A vehicle as set forth in claim 1 wherein said optical source and at least said plurality of radiation detector means are located within said sampling means.

13. A vehicle that generates a gas comprised of a plurality of different chemical species, the vehicle comprising:

means for sampling at least a portion of the gas, said sampling means having an optical input port and an optical output port;

an optical source having an output coupled to said optical input port of said sampling means, said optical source generating electromagnetic radiation having wavelengths that are absorbed by predetermined ones of the chemical species; and a plurality of radiation detector means individual ones of which have an input coupled to said optical output port of said sampling means, individual ones of said radiation detector means being responsive to a band of wavelengths that includes wavelengths that are absorbed by at least one of the predetermined ones of the chemical species for determining an amount of the electromagnetic radiation, within the band of wavelengths, that is transmitted through the gas within said sampling means;

wherein said sampling means is comprised of a sampling cell having at least one window that is substantially transparent to the electromagnetic radiation having wavelengths that are absorbed by predetermined ones of the chemical species; and further comprising means for removing an accumulation of an emission gas constituent from said window.

14. A spectroscopic system, comprising:

means for sampling a gas or a liquid that is comprised of a plurality of different chemical species, said sampling means having an optical input port and an optical output port;

an optical source having an output coupled to said optical input port of said sampling means, said optical source generating electromagnetic radiation having wavelengths that are absorbed by predetermined ones of the chemical species; and a plurality of radiation detector means individual ones of which have an input coupled to said optical output port of said sampling means, individual ones of said radiation detector means being responsive to a band of wavelengths that includes wavelengths that are absorbed by at least one of the predetermined ones of the chemical species for determining an amount of the electromagnetic radiation, within the band of wavelengths, that is transmitted through the sample within said sampling means, wherein individual ones of said radiation detector means are comprised of a radiation detector device that is fabricated within or upon a surface of a common substrate, and further comprising a plurality of amplifier circuits individual ones of which have an input coupled to an output of one of said radiation detector devices, said plurality of amplifier circuits also being fabricated within or upon the surface of said common substrate; and wherein individual ones of said radiation detector means are further comprised of an input filter for passing wavelengths within the band of wavelengths, said input filter being a multi-layered filter that is deposited upon a radiation receiving surface of said radiation detector device.

15. A spectrographic system as set forth in claim 14 wherein individual ones of said radiation detector means are comprised of a thermopile radiation detector that is fabricated within or upon a surface of the common substrate.

16. A spectrographic system as set forth in claim 14 and further comprising:

a multiplexer circuit having a plurality of inputs individual ones of which are coupled to an output of one of said amplifier circuits;

an analog to digital converter having an input coupled to an output of said multiplexer circuit; and processor means having an input coupled to an output of said analog to digital converter for determining a concentration of the predetermined ones of the chemical species within the sample, wherein at least said multiplexer circuit and said analog to digital converter are fabricated within or upon the surface of the common substrate.

17. A spectrographic system as set forth in claim 14 wherein said optical source generates electromagnetic radiation having wavelengths within a least one spectral band selected from the group consisting of the ultraviolet spectral band, the visible spectral band, the infrared spectral band, and the far infrared spectral band.

18. A spectrographic system as set forth in claim 14 and further comprising means, coupled to said output port, for diffusing the electromagnetic radiation that passes through said output port.

19. A spectrographic system as set forth in claim 14 wherein said sampling means includes at least one window that is substantially transparent to the electromagnetic radiation having wavelengths that are absorbed by predetermined ones of the chemical species.

20. A spectrographic system as set forth in claim 19 and further comprising means for retarding an accumulation of a constituent of said gas or liquid upon said at least one window.

21. A spectrographic system comprising:

means for sampling a gas or a liquid that is comprised of a plurality of different chemical species, said sampling means having an optical input port and an optical output port;

an optical source having an output coupled to said optical input port of said sampling means, said optical source generating electromagnetic radiation having wavelengths that are absorbed by predetermined ones of the chemical species; and a plurality of radiation detector means individual ones of which have an input coupled to said optical output port of said sampling means, individual ones of said radiation detector means being responsive to a band of wavelengths that includes wavelengths that are absorbed by at least one of the predetermined ones of the chemical species for determining an amount of the electromagnetic radiation, within the band of wavelengths, that is transmitted through the sample within said sampling means, wherein individual ones of said radiation detector means are comprised of a radiation detector device that is fabricated within or upon a surface of a common substrate, and further comprising a plurality of amplifier circuits individual ones of which have an input coupled to an output of one of said radiation detector devices, said plurality of amplifier circuits also being fabricated within or upon the surface of said common substrate;

wherein said sampling means includes at least one window that is substantially transparent to the electromagnetic radiation having wavelengths that are absorbed by predetermined ones of the chemical species;

and further comprising means for removing an accumulation of a constituent of said gas or liquid from said at least one window.

22. An electronic component for use in detecting a concentration of individual ones of a plurality of chemical species, comprising:

an optical input port;

a substrate;

a plurality of radiation detector means individual ones of which have an input coupled to said optical input port, individual ones of said radiation detector means being responsive to a band of wavelengths that includes wavelengths that are absorbed by at least one of the predetermined ones of the chemical species, individual ones of said radiation detector means being comprised of a radiation detector device that is fabricated within or upon a surface of the substrate; and a plurality of amplifier circuits individual ones of which have an input coupled to an output of one of said radiation detector devices, said plurality of amplifier circuits also being fabricated within or upon the surface of said substrate;

wherein individual ones of said radiation detector means are further comprised of an input filter for passing wavelengths within the band of wavelengths, said input filter being a multi-layered filter that is deposited upon a radiation receiving surface of said radiation detector device.

23. An electronic component as set forth in claim 22 wherein individual ones of said radiation detector means are further comprised of a selectively absorbing film for absorbing incident electromagnetic radiation.

24. An electronic component as set forth in claim 22 wherein individual ones of said radiation detector means are comprised of a thermopile radiation detector that is fabricated within or upon a surface of the substrate.

25. An electronic component as set forth in claim 22 and further comprising:

a multiplexer circuit having a plurality of inputs individual ones of which are coupled to an output of one of said amplifier circuits;

an analog to digital converter having an input coupled to an output of said multiplexer circuit; and processor means having an input coupled to an output of said analog to digital converter for determining a concentration of the predetermined ones of the chemical species within a sample, wherein at least said multiplexer circuit and said analog to digital converter are fabricated within or upon the surface of the substrate.

26. An electronic component as set forth in claim 22 wherein individual ones of said radiation detector means are responsive to electromagnetic radiation having wavelengths within a spectral band selected from the group consisting of the ultraviolet spectral band, the visible spectral band, the infrared spectral band, and the far infrared spectral band.

27. An electronic component as set forth in claim 22 wherein at least one of said radiation detector means is responsive to electromagnetic radiation that is absorbed by CO.

28. An electronic component as set forth in claim 22 wherein at least one of said radiation detector means is responsive to electromagnetic radiation that is absorbed by hydrocarbons.

29. An electronic component as set forth in claim 22 wherein at least one of said radiation detector means is responsive to electromagnetic radiation that is absorbed by $CO_2$.

30. An electronic component as set forth in claim 22 wherein at least one of said radiation detector means is responsive to electromagnetic radiation that is absorbed by NO.

31. An electronic component as set forth in claim 22 wherein at least one of said radiation detector means is responsive to electromagnetic radiation that is absorbed by $H_2O$.

32. An electronic component as set forth in claim 22 wherein at least one of said radiation detector means is responsive to electromagnetic radiation that is not strongly absorbed by any of the plurality of chemical species.

33. An electronic component as set forth in claim 22 and further comprising a plurality of input/output terminals, at least one of said terminals being coupled to means for providing a data output from said electronic component, the data output being expressive of an amount of electromagnetic radiation that is detected by individual ones of said plurality of radiation detector means.

34. A multispectral sensor system for sensing one or more different chemical species within a flow, comprising:

means for sampling at least a portion of the flow, said sampling means having an optical input port and an optical output port;

an optical source having an output coupled to said optical input port of said sampling means, said optical source generating electromagnetic radiation having wavelengths that are absorbed by predetermined ones of the chemical species; and a monolithic sensor assembly comprised of a plurality of radiation detector means individual ones of which have an input coupled to said optical output port of said sampling means, individual ones of said radiation detector means being responsive to a band of wavelengths that includes wavelengths that are absorbed by at least one of the predetermined ones of the chemical species for determining an amount of the electromagnetic radiation, within the band of wavelengths, that is transmitted through the sampled portion of the flow;

wherein individual ones of said radiation detector means are fabricated upon or within a surface of a common substrate and are comprised of a radiation detector device having an integral input filter for passing wavelengths within the band of wavelengths, said integral input filter being deposited upon a radiation receiving surface of said radiation detector device.

35. A sensor system as set forth in claim 34 and further comprising processor means having an input coupled to an output of said plurality of radiation detector means for determining a concentration of predetermined ones of the chemical species.

36. A sensor system as set forth in claim 34, and further comprising a plurality of amplifier circuits individual ones of which have an input coupled to an output of one of said radiation detector devices, said plurality of amplifier circuits being fabricated within or upon the surface of said common substrate.

37. A sensor system as set forth in claim 34 wherein individual ones of said integral input filters are a multi-layered filter that is deposited upon said radiation receiving surface of said radiation detector device.

38. A sensor system as set forth in claim 34 wherein individual ones of said radiation detector means are further comprised of a multilayer selectively absorbing dark film.

39. A sensor system as set forth in claim 34 wherein individual ones of said radiation detector means are comprised of a thermopile radiation detector that is fabricated within or upon a surface of said common substrate.

40. A sensor system as set forth in claim 34 wherein said optical source generates electromagnetic radiation having wavelengths within a least one spectral band selected from the group consisting of the ultraviolet spectral band, the visible spectral band, the infrared spectral band, and the far infrared spectral band.

41. A sensor system as set forth in claim 34 and further comprising means, coupled to said output port, for diffusing electromagnetic radiation that passes through said output port.

42. A sensor system as set forth in claim 34 wherein said sampling means is comprised of a sampling cell having at least one window that is substantially transparent to the electromagnetic radiation having wavelengths that are absorbed by predetermined ones of the chemical species.

43. A sensor system as set forth in claim 42 and further comprising means for retarding an accumulation of a flow constituent upon said window.

44. A sensor system as set forth in claim 34 wherein said sampling means has a plurality of apertures for forming said input port and said output port.

45. A sensor system as set forth in claim 34 wherein said optical source and at least said plurality of radiation detector means are located within said sampling means.

46. A multispectral sensor system for sensing one or more different chemical species within a flow, comprising:

means for sampling at least a portion of the flow, said sampling means having an optical input port and an optical output port;

an optical source having an output coupled to said optical input port of said sampling means, said optical source generating electromagnetic radiation having wavelengths that are absorbed by predetermined ones of the chemical species; and a monolithic sensor assembly comprised of a plurality of radiation detector means individual ones of which have an input coupled to said optical output port of said sampling means, individual ones of said radiation detector means being responsive to a band of wavelengths that includes wavelengths that are absorbed by at least one of the predetermined ones of the chemical species for determining an amount of the electromagnetic radiation, within the band of wavelengths, that is transmitted through the sampled portion of the flow;

wherein said sampling means is comprised of a sampling cell having at least one window that is substantially transparent to the electromagnetic radiation having wavelengths that are absorbed by predetermined ones of the chemical species;

and further comprising means for removing an accumulation of a flow constituent from said window.

* * * * *